(12) United States Patent
Beebe et al.

(10) Patent No.: US 8,328,757 B2
(45) Date of Patent: Dec. 11, 2012

(54) BLADDER ARRANGEMENT FOR MICRONEEDLE-BASED DRUG DELIVERY DEVICE

(75) Inventors: David J. Beebe, Monona, WI (US); Benjamin J. Moga, Madison, WI (US); Kent B. Chase, Sun Prairie, WI (US); Garrick D. S. Smith, Madison, WI (US); Jake W. Myre, Beaver Dam, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 12/684,566

(22) Filed: Jan. 8, 2010

(65) Prior Publication Data

US 2011/0172601 A1  Jul. 14, 2011

(51) Int. Cl.
*A61M 37/01* (2006.01)
(52) U.S. Cl. ........................................ 604/131
(58) Field of Classification Search .................. 604/132, 604/133, 131
See application file for complete search history.

(56) References Cited

U.S. PATENT DOCUMENTS

| | | | |
|---|---|---|---|
| 3,469,578 A * | 9/1969 | Bierman | 604/132 |
| 4,552,561 A | 11/1985 | Eckenhoff et al. | |
| 4,556,086 A | 12/1985 | Raines | |
| 5,109,850 A | 5/1992 | Blanco et al. | |
| 5,169,389 A * | 12/1992 | Kriesel | 604/132 |
| 5,224,843 A | 7/1993 | Van Lintel | |
| 5,346,476 A * | 9/1994 | Elson | 604/135 |
| 5,466,261 A | 11/1995 | Richelsoph | |
| 5,693,018 A * | 12/1997 | Kriesel et al. | 604/132 |
| 5,716,343 A * | 2/1998 | Kriesel et al. | 604/132 |
| 5,785,688 A | 7/1998 | Joshi et al. | |
| 5,848,991 A * | 12/1998 | Gross et al. | 604/140 |
| 5,921,962 A * | 7/1999 | Kriesel et al. | 604/132 |
| 5,928,194 A | 7/1999 | Maget | |
| 5,935,593 A | 8/1999 | Ron et al. | |
| 6,068,613 A * | 5/2000 | Kriesel et al. | 604/132 |
| 6,268,161 B1 | 7/2001 | Han et al. | |
| 6,416,495 B1 | 7/2002 | Kriesel et al. | |
| 6,475,750 B1 | 11/2002 | Han et al. | |
| 6,485,461 B1 | 11/2002 | Mason et al. | |
| 6,514,689 B2 | 2/2003 | Han et al. | |
| 6,523,559 B2 | 2/2003 | Beebe et al. | |
| 6,689,100 B2 | 2/2004 | Connelly et al. | |
| 7,074,915 B2 | 7/2006 | Soreq et al. | |
| 7,115,108 B2 * | 10/2006 | Wilkinson et al. | 604/93.01 |
| 7,156,838 B2 * | 1/2007 | Gabel et al. | 604/890.1 |
| 7,410,476 B2 * | 8/2008 | Wilkinson et al. | 604/93.01 |
| 2002/0063060 A1 | 5/2002 | Gascoyne et al. | |
| 2002/0117517 A1 | 8/2002 | Unger et al. | |
| 2002/0193729 A1 | 12/2002 | Cormier et al. | |
| 2003/0187423 A1 * | 10/2003 | Wilkinson et al. | 604/506 |
| 2003/0196900 A1 * | 10/2003 | Chuang et al. | 204/600 |
| 2004/0068224 A1 | 4/2004 | Couvillon et al. | |
| 2004/0248326 A1 | 12/2004 | Ziaie et al. | |
| 2005/0038379 A1 | 2/2005 | Beebe et al. | |
| 2006/0002804 A1 | 1/2006 | Jiang et al. | |
| 2006/0116664 A1 | 6/2006 | Richter et al. | |
| 2007/0250018 A1 | 10/2007 | Adachi et al. | |
| 2009/0306594 A1 * | 12/2009 | Pang et al. | 604/133 |
| 2009/0312742 A1 * | 12/2009 | Pang et al. | 604/500 |
| 2010/0179473 A1 * | 7/2010 | Genosar | 604/70 |

* cited by examiner

*Primary Examiner* — Nicholas Lucchesi
*Assistant Examiner* — Diva K Chander
(74) *Attorney, Agent, or Firm* — Boyle Fredrickson, S.C.

(57) ABSTRACT

A bladder arrangement is provided for a microneedle-based drug delivery device. The bladder arrangement includes a flexible membrane having an inner surface, an outer surface and an outer periphery. A bladder member, having a rigidity greater than the flexible membrane, includes an inner surface, an outer surface and an outer periphery. The inner surface of the flexible membrane and the inner surface of the bladder member define a chamber for receiving a drug therein. At least one microneedle is operatively connected to the bladder member. The at least one microneedle has an input and an output receivable within the individual. A valve operatively connects the input of the at least one microneedle and the chamber.

14 Claims, 4 Drawing Sheets

BLADDER ARRANGEMENT FOR MICRONEEDLE-BASED DRUG DELIVERY DEVICE

FIELD OF THE INVENTION

This invention relates generally to drug delivery devices, and in particular, to a bladder arrangement for a microneedle-based, active transdermal drug delivery device that allows for the delivery of a steady infusion of a pharmaceutical to an individual.

BACKGROUND AND SUMMARY OF THE INVENTION

As is known, the pharmaceutical industry has had limited success overcoming the challenges of delivering pharmaceuticals to patients. The oral ingestion of pharmaceuticals is considered the safest, most convenient and most economical method of drug administration. As compared to present alternatives, patient acceptance and adherence to a dosing regimen is typically higher among orally delivered pharmaceuticals. However, the oral delivery of many pharmaceuticals is not possible because the pharmaceutical molecule is either too large or too electrically charged to pass through the small intestine to reach the bloodstream. In addition, many pharmaceuticals that are unable to withstand the environment of the digestive tract or to penetrate the dermis need to be injected into the patient (e.g. insulin, proteins). As hereinafter described, the injection of pharmaceuticals into a patient has certain drawbacks.

By way of example, insulin is often used to treat diabetes, a disorder of metabolism. Most of the foods eaten by individuals are broken down in the body into glucose, the form of sugar in the blood. Glucose is the main source of fuel for the body. After digestion, the glucose passes into the bloodstream where it is used by the cells for growth and energy. For glucose to get into cells, insulin must be present. Insulin is a hormone that is automatically produced by a healthy pancreas to move glucose from blood into our cells. In people with diabetes, however, the pancreas either produces little or no insulin, or the cells do not respond appropriately to the insulin that is produced. As a result, glucose builds up in the blood, overflows into the urine, and passes out of the body. Consequently, the body loses its main source of fuel, even though the blood contains large amounts of glucose.

In order to use the glucose present in the body, a diabetic must take insulin injections every day. The amount of insulin taken by an individual must be balanced with the individual's food intake and daily activities. Consequently, blood glucose levels must be closely monitored through frequent blood glucose checking to insure that blood glucose levels do not fall too low or rise too high. When blood glucose levels drop too low from certain diabetes medicines—a condition known as hypoglycemia—a person can become nervous, shaky, and confused. If blood glucose falls, judgment can be impaired and a person could faint. Alternatively, a person can also become ill if blood glucose levels rise too high, a condition known as hyperglycemia. Although daily insulin injections are a great inconvenience, they are necessary for a diabetics' survival.

Most people with diabetes administer their own insulin after learning the proper techniques for insulin preparation and injection. The goal of insulin administration is to give enough insulin to cover the amount of food (especially carbohydrates) that a person consumes so that blood glucose levels remain normal throughout the day and night. It can be appreciated that various factors such as the type of insulin used, the size of the person, the amount, type, and time that meals are eaten, and the activity and exercise patterns of the person affect the amount of insulin that is required by an individual. It takes a dedicated patient to continually monitor their blood glucose level and administer the repeated multiple injections required. Therefore, an autonomous infusion system that provides a steady infusion of pharmaceuticals to an individual when needed would constitute a significant advancement in the art.

Therefore, it is a primary object and feature of the present invention to provide a bladder arrangement for a microneedle-based, active transdermal drug delivery device that allows for the delivery of a steady infusion of a pharmaceutical to an individual when needed.

It is a further object and feature of the present invention to provide a bladder arrangement for a microfluidic, drug delivery device that allows for the delivery of a infusion of a pharmaceutical to an individual that is simple to utilize and inexpensive to manufacture.

In accordance with the present invention, a bladder arrangement is provided for a microfluidic drug delivery device. The bladder arrangement includes a first flexible membrane having an inner and outer surface. A rigid bladder member includes an inner surface and an outer surface. The inner surface of the flexible membrane and the inner surface of the rigid bladder member defines a chamber for receiving a drug therein. The bladder arrangement further includes at least one microneedle and a valve arrangement operatively connecting the at least one microneedle to the rigid bladder member. The valve arrangement has a first configuration wherein the at least one microneedle is fluidically isolated from the drug in the chamber and a second configuration wherein the at least one microneedle fluidically communicates with the drug in the chamber.

The first flexible membrane has an outer periphery and the rigid bladder member has an outer periphery. The outer periphery of the first flexible membrane and the outer periphery of the rigid bladder member are bonded to form a hermetic tight seal. It is contemplated for the at least one microneedle is one of an array of microneedles. The rigid bladder matter includes an opening therethrough for allowing the drug to be injected into the chamber. A plug is receivable in the opening in the rigid bladder matter for maintaining the drug in the chamber. The valve arrangement may include a check valve. The check valve allows the drug to flow in a first direction from the chamber to the at least one microneedle and prevents fluid flow in a second direction from the at least one microneedle to the chamber.

In accordance with a further aspect of the present invention, a bladder arrangement is provided for a microfluidic drug delivery device. The bladder arrangement includes a flexible membrane having an inner surface, an outer surface and an outer periphery. A rigid bladder member includes an inner surface, an outer surface and an outer periphery bonded to the outer periphery of the flexible membrane. The inner surface of the flexible membrane and the inner surface of the rigid bladder member define a chamber for receiving a drug therein. At least one microneedle is operatively connected to the rigid bladder member. A valve arrangement controls the flow of the drug from the chamber to the at least one microneedle.

The outer periphery of the flexible membrane and the outer periphery of the rigid bladder member are bonded to form a hermetic seal. It is contemplated for the at least one microneedle to be one of an array of microneedles. The rigid bladder member includes an opening therethrough for allowing the drug to be injected into the bladder and wherein the bladder arrangement further comprises a plug receivable in the opening in the rigid bladder matter for maintaining the drug in the chamber. The valve arrangement includes a check valve. The check valve allows the drug to flow in a first direction from the chamber to the at least one microneedle and preventing fluid flow in a second direction from the at least one microneedle to the chamber. A pressure source is engageable with the flexible member for urging the drug from the chamber to the at least one microneedle. The pressure source includes an expandable hydrogel. The hydrogel applies pressure on the flexible member as the hydrogel expands.

In accordance with a still further aspect of the present invention, a bladder arrangement is provided for a microfluidic drug delivery device. The bladder arrangement includes a flexible membrane having an inner surface, an outer surface and an outer periphery. A rigid bladder member includes an inner surface, an outer surface and an outer periphery. The inner surface of the flexible membrane and the inner surface of the rigid bladder member define a chamber for receiving a drug therein. At least one microneedle is operatively connected to the rigid bladder member. The at least one microneedle has an input and an output receivable within the individual. A valve is operatively connected the input of the at least one microneedle and the chamber.

A pressure source is engageable with the flexible membrane for urging the drug from the chamber through the at least one microneedle. The outer periphery of the flexible membrane and the outer periphery of the rigid bladder member are bonded to form a hermetic tight seal. The at least one microneedle is one of an array of microneedles and the rigid bladder matter may include an opening therethrough for allowing the drug to be injected into the chamber. A plug is receivable in the opening in the rigid bladder member for maintaining the drug in the chamber. It is contemplated for the valve to be a check valve. The check valve allows the drug to flow in a first direction from the chamber to the at least one microneedle and prevents fluid flow in a second direction from the at least one microneedle to the chamber. A docking station may be used to support the at least one microneedle. The docking station is removably connected to the rigid bladder member.

BRIEF DESCRIPTION OF THE DRAWINGS

The drawings furnished herewith illustrate a preferred construction of the present invention in which the above advantages and features are clearly disclosed as well as other which will be readily understood from the following description of the illustrated embodiments.

In the drawings.

DETAILED DESCRIPTION OF THE DRAWINGS

Figure 1:
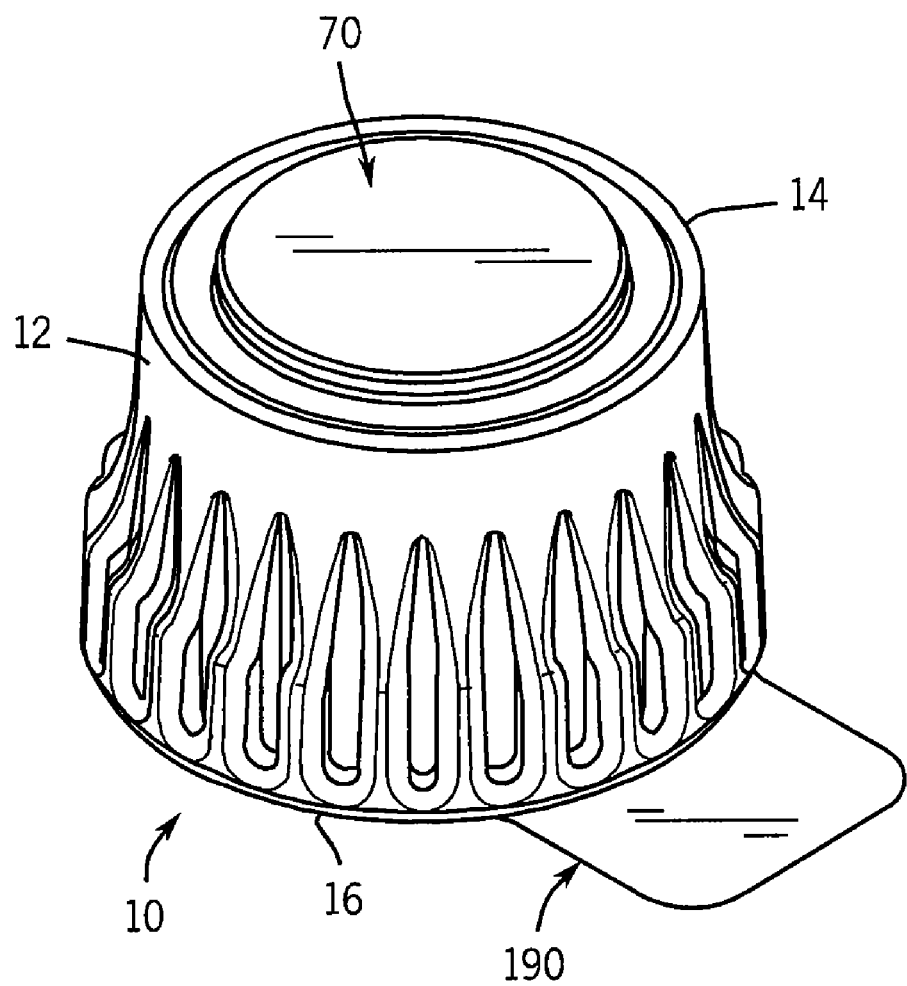
FIG. 1 is an isometric view of a drug delivery device incorporating a bladder arrangement in accordance with the present invention.
Figure 2:
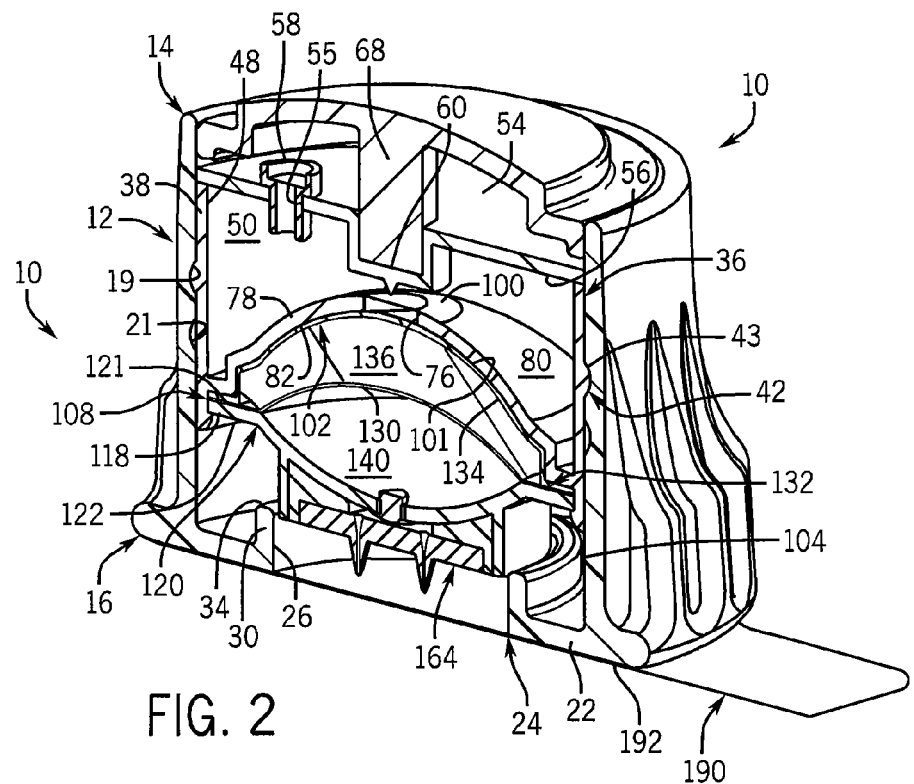
FIG. 2 is a schematic, isometric view of a cross-section of the microfluidic device in a non-actuated position taken along line 2-2 of FIG. 1.
Figure 3:
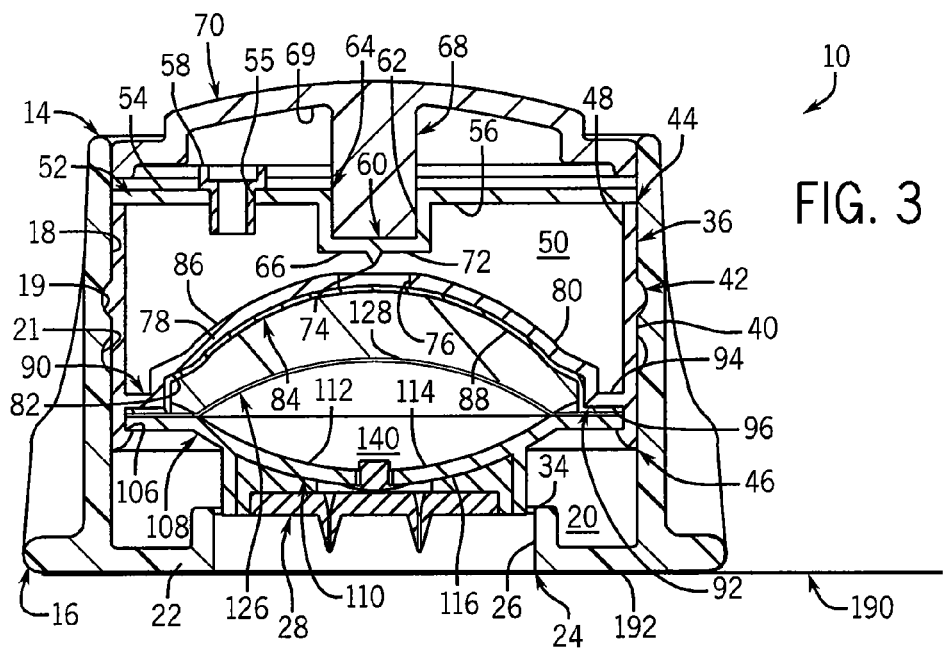
FIG. 3 is a schematic, cross-sectional view of the microfluidic device of FIG. 2 in the non-actuated position.

Referring to FIG. 1, a microfluidic device incorporating a bladder arrangement in accordance with the present invention is generally designated by the reference numeral 10. Microfluidic device 10 includes body 12 having a generally cylindrical configuration with first and second opposite ends 14 and 16, respectively. As best seen in FIGS. 2-3, body 12 includes inner surface 18 defining cavity 20. Inner surface 18 of body 12 includes upper and lower vertically spaced grooves 19 and 21, respectively, for reasons hereinafter described. Lower wall 22 projects radially inward from second end 16 of body 12 and terminates at radially inner edge 24. Inner edge 24 of lower wall 22 defines an opening 26 for receiving docking station 154, FIGS. 4-5, as hereinafter described. Inner wall 30 projects vertically from inner edge 24 of lower wall 22 and terminates at terminal end 34.

Fluid container 36 is slidably received in cavity 20. Fluid container 36 has a generally cylindrical outer wall 38 defining an outer surface 40 that forms a slideable interface with inner surface 18 of body 12. Detent 42 projects radially outward from outer surface 40 of fluid container 36 and is defined by an arcuate engaging surface 43 adapted for receipt in one of upper and lower vertically spaced grooves 19 and 21, respectively. Outer wall 38 of fluid container 36 is further defined by upper end 44, lower end 46 and inner surface 48. Inner surface 48 of outer wall 38 partially defines a chamber 50 for receiving an initiation fluid therein.

Upper wall 52 of fluid container 36 extends radially inward from upper end 44 of outer wall 38 and is defined by upper and lower surfaces 54 and 56, respectively. Filling aperture 55 extends between upper and lower surfaces 54 and 56, respectively, of upper wall 48 to allow chamber 50 to be filled with the initiation fluid therethrough. Plug 58 may be inserted into filling aperture 55 to seal filling aperture 55 and prevent the initiation fluid from passing back therethrough after the filling of chamber 50. In addition, it is contemplated for plug 58 to function as a vent to relieve the buildup of pressure in chamber 50 during operation of device 10. Upper surface 54 of upper wall 52 includes a centrally located depression 60 therein formed from a resilient material. Depression 60 is defined by generally cylindrical sidewall 62 depending from radially inner edge 64 of upper wall 52 and terminal wall 66 which closes depression 60. Depression 60 is adapted to receiving plunger 68 depending from lower surface 69 of pushbutton 70. Lower surface 72 of terminal wall 66 includes a centrally located pin 74 depending therefrom. Pin 74 is axially aligned with aperture 76 which is centrally located through lower wall 78 of fluid container 36 between upper and lower surfaces 80 and 82, respectively, thereof.

Lower wall 78 of fluid container 36 extends radially inward from outer wall 38 at a location spaced from lower end 46 thereon. Lower wall 78 includes central portion 84 having a generally convex upper surface 86 and a generally concave lower surface 88. Outer portion 90 of lower wall 78 extends radially outward from radially outer edge 92 of central portion 84 of lower wall 78 to inner surface 48 of outer wall 38. Outer portion 90 of lower wall 78 includes a generally flat, ring shaped upper surface 94 and a generally flat, ring shaped lower surface 96. Upper surface 86 of central portion 84 and upper surface 94 of outer portion 90 define upper surface 80 of lower wall 78. Lower surface 88 of central portion 84 and lower surface 96 of outer portion 90 define lower surface 82 of lower wall 78. As previously noted, lower wall 78 of fluid container 36 includes a centrally located aperture 76 which is axially aligned with pin 74 depending from lower surface 72 of terminal wall 66. First disc-shaped membrane 100 is affixed to upper surface 86 of central portion 84 of lower wall 78 so as to overlap aperture 76 and prevent the initiation fluid in chamber 50 from flowing therethrough. Upper surface 101 of wicking material 102 is affixed to the entirety of lower surface 82 of lower wall 78 of fluid container 36.

Lower end 46 of outer wall 38 of fluid container 36 includes tang 104 extending radially inward therefrom and having an upper surface 106 adapted for receiving the outer periphery of bladder arrangement 108, hereinafter described. Bladder arrangement 108 includes rigid bladder member 110 having a central portion 112 defined by a generally concave upper surface 114 and a generally convex lower surface 116. It is contemplated for rigid bladder member 110 to be somewhat flexible, but have a rigidity greater than the rigidity of flexible membrane 126, hereinafter described. Generally flat outer portion 118 of rigid bladder member 110 extends radially outward from radially outer edge 120 of central portion 112 of rigid bladder member 110. Outer portion 118 of rigid bladder member 110 includes a generally flat, ring shaped upper surface 121 and a generally flat, ring shaped lower surface 122.

Bladder arrangement 108 further includes flexible membrane 126 having upper surface 128 and lower surface 130. Outer periphery 132 of lower surface 130 of flexible membrane 126 is bonded to upper surface 121 of outer portion 118 of rigid bladder member 110 to form a hermetic seal. Upper surface 128 of flexible membrane 126 and lower surface 134 of wicking material 102 define chamber 136 for receiving hydrogel pressure source 138, FIG. 4, therein. Lower surface 130 of flexible member 126 and upper surface 114 of rigid bladder member 110 define chamber 140 for receiving a fluid such as a drug or a pharmaceutical to be administered to a patient. Lower surface 122 of outer portion 118 of rigid bladder member 110 is received on and supported by upper surface 106 of tang 104 so as to capture the outer peripheries of flexible membrane 126 and wicking material 102 between upper surface 121 of outer portion 118 of rigid bladder member 110 and lower surface 96 of outer portion 90 of lower wall 78.

Figure 4:
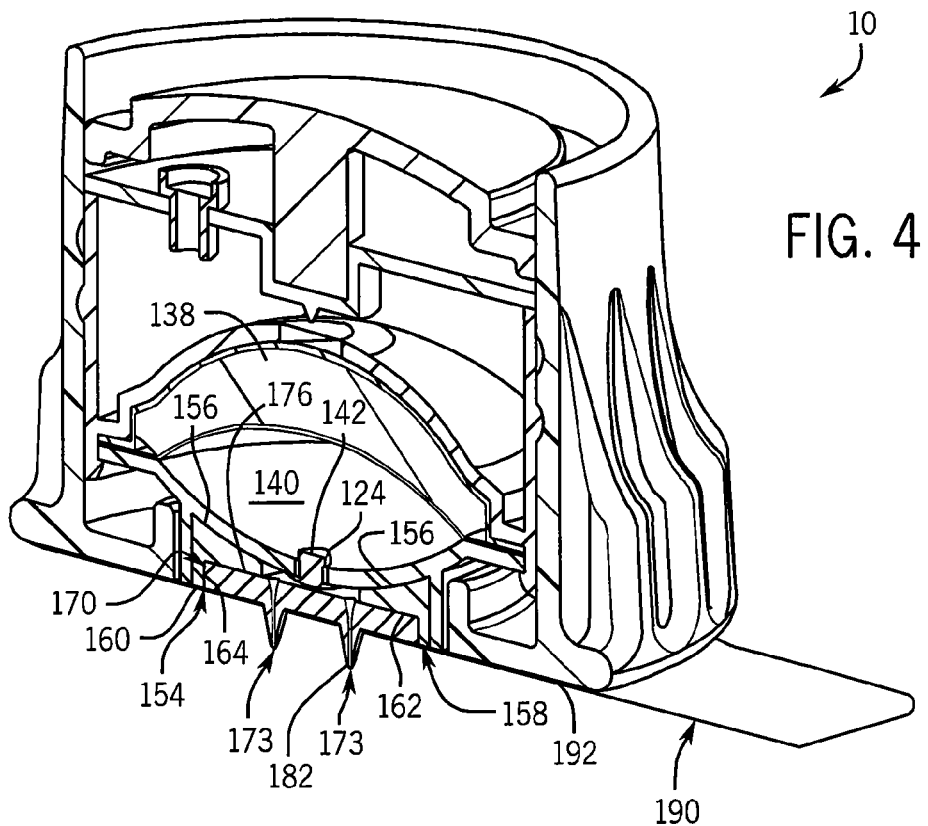
FIG. 4 is a schematic, isometric view of a cross-section, similar to FIG. 2, showing the microfluidic device in a first actuated position.
Figure 5:
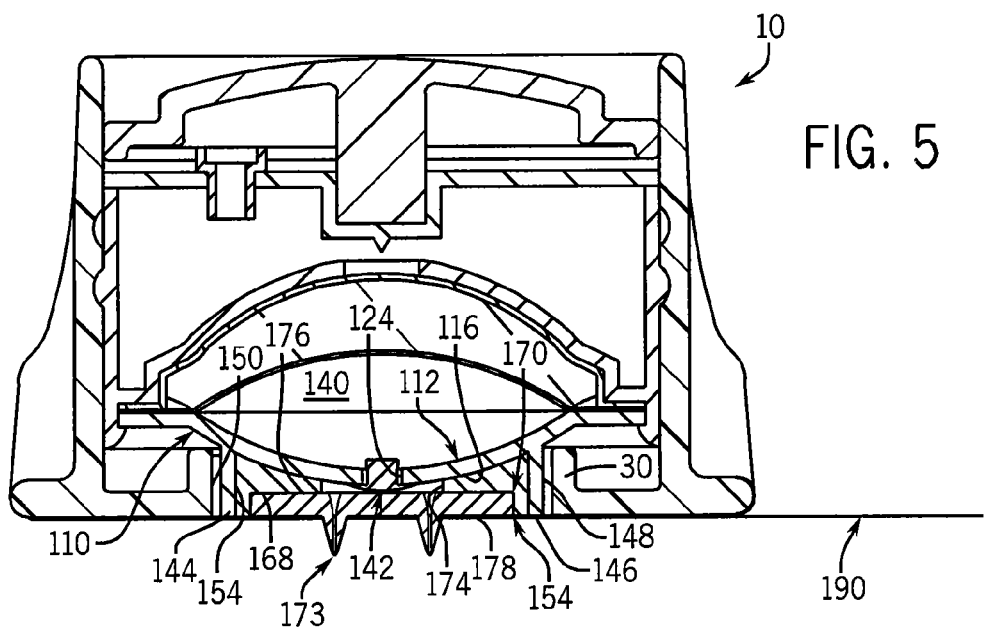
FIG. 5 is a schematic, cross-sectional view of the microfluidic device of FIG. 4 in the first actuated position.

Referring to FIGS. 4-5, central portion 112 of rigid bladder member 110 includes a centrally located aperture 124 therethrough to allow chamber 140 to be filled with the fluid to be administered. After filling, it is contemplated to provide check valve 142 in aperture 124. Optionally, second aperture 139 and plug 141 combination may be provided in rigid bladder member 110 to allow chamber 140 to be filled with the fluid to be administered, FIG. 7. Check valve 142 prevents additional fluid to be injected into chamber 140. In order for the fluid to be administered to be discharged from chamber 140 and pass through check valve 142, the pressure of the fluid in chamber 140 must exceed a threshold.

Support 144 depends from lower surface 116 of central portion 112 of rigid bladder member 110 and terminates at terminal end 146. Support 144 includes outer surface 148 which forms a slidable interface with inner surface 150 of inner wall 30 of body 12 and inner surface 152 adapted for supporting docking station 154. Docking station 154 includes upper surface 156 engageable with lower surface 116 of central portion 112 of rigid bladder member 110 and lower surface 158. Lower surface 158 includes outer portion 160 which is substantially flush with terminal end 146 of support 144 and recessed portion 162 which is spaced from outer portion 160 by sidewall 164. Passageway 174 extends between recessed portion 162 of lower surface 158 of docking station 154 and upper surface 156 of docking station 154.

Figure 6:
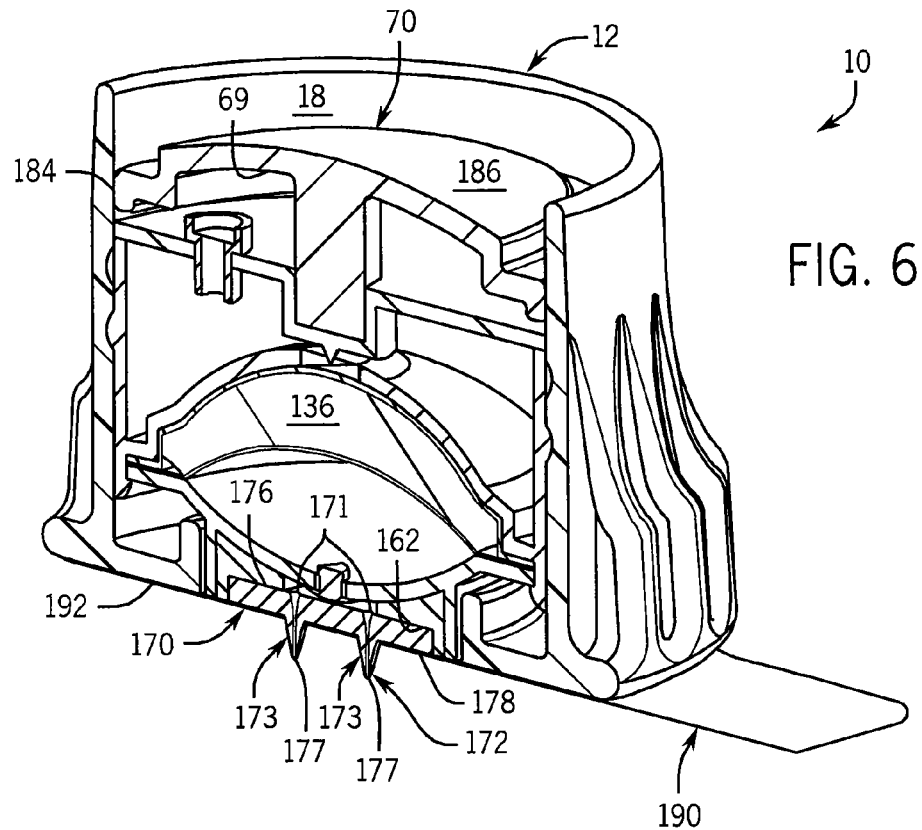
FIG. 6 is a schematic, isometric view of a cross-section, similar to FIG. 2, showing the microfluidic device in a second actuated position.
Figure 7:
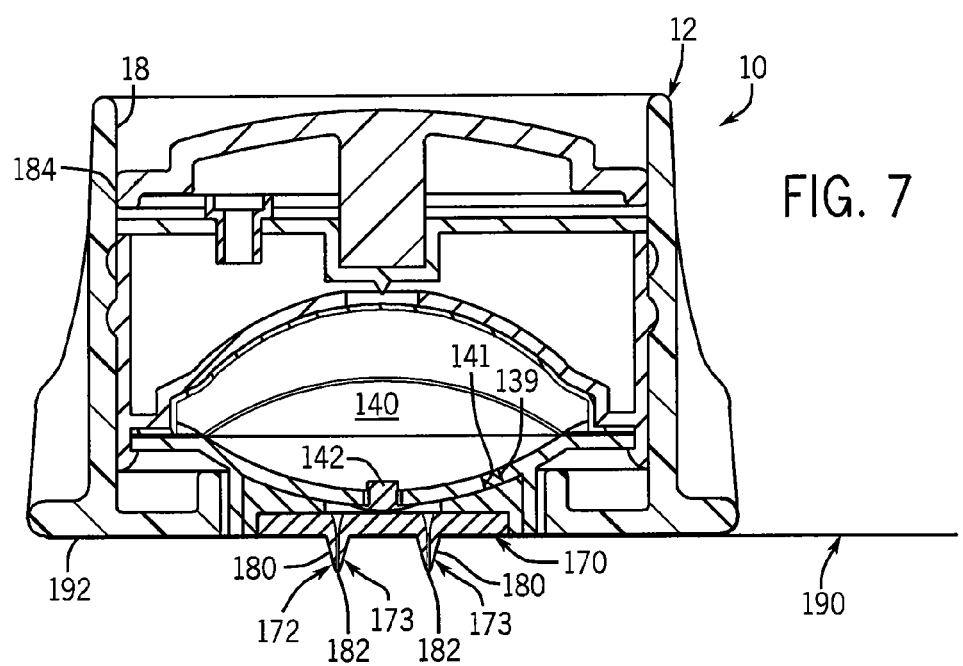
FIG. 7 is a schematic, cross-sectional view of the microfluidic device of FIG. 6 in the second actuated position.

Recessed portion 162 of lower surface 158 and sidewall 164 define cavity 168 adapted for receiving microneedle structure 170. Referring to FIGS. 6-7, microneedle structure 170 includes upper surface 176 engageable with recessed portion 162 of lower surface 158 of docking station 154, lower surface 178 substantially flush with outer portion 160 of lower surface 158 of docking station 154, and an array of microneedles 172. Each microneedle 173 of array of microneedles 172 has an input 171 communicating with passageway 174, and hence, the output of check valve 142, and an output 177. In addition, each microneedle 173 includes generally conical outer surface 180 terminating at tip 182. It is intended for tip 182 to penetrate the skin of an individual to which the fluid is to be administered.

In order to actuate microfluidic device 10, pushbutton 70 is provided. Pushbutton 70 is generally disc-shaped and includes outer periphery 184 which forms a slideable interface with inner surface 18 of body 12. Outer periphery 184 of pushbutton 70 interconnects lower surface 69 of pushbutton with upper surface 186 thereof. In operation, detent 42 is seated in upper groove 19 in inner surface 18 of body 12. Chamber 50 of fluid container 36 is filled through filling aperture 55 in upper wall 52 of fluid container 36 and plug 58 is inserted into filling aperture 55 to retain the initiation fluid therein. Chamber 136 is filled with hydrogel pressure source 138 that expands in response to exposure to the initiation fluid and chamber 140 is filled with the fluid to be administered to a patient. Lower surface 192 of lower wall 22 of body 12 is affixed to the patient as a desired location by means of adhesive pad 190 or the like affixed to lower surface 192 of lower wall 22 of body 12.

Once the microfluidic device 10 is affixed to the patient at the desired location, FIGS. 2-3, pushbutton 70 is depressed so as to urge plunger 68 against the bias of depression 60 in upper wall 52 such that resilient material from which depression 60 is fabricated flexes downwardly, FIGS. 6-7. Pin 74, depending from lower surface 72 of terminal wall 66, engages first membrane 100 so as to burst first and second membrane 100. As a result, the initiation fluid is free to flow through aperture 76 in lower wall 78 from chamber 50 into chamber 136 filled with the hydrogel pressure source 138.

As a user continues to depress pushbutton 70, FIGS. 4-5, fluid container 36 is urged downwardly within body 12 such that detent 42 becomes seated in lower groove 21 in inner surface 18 of body 12. As fluid container 36 moves downwardly, bladder arrangement 108 is urged downwardly such that support 144 slides along with inner surface 150 of inner wall 30 of body 12 until lower surface 116 of central portion 112 of rigid bladder member 110 engages terminal end 34 of lower wall 24 of body 12. With bladder arrangement in its lowered configuration, tips 182 of microneedles 173 penetrate the patient and are in communication with the dermal layer of the patient. As the initiation fluid flows through aperture 76 in lower wall 78 from chamber 50 into chamber 136, hydrogel pressure source 138 in chamber 136 expands thereby providing pressure onto flexible membrane 126. Under pressure, the fluid in chamber 140 is urged through check valve 142 such that the fluid flows into passageway 174, and hence, into inputs 171 of microneedles 173. Thereafter, the fluid exits outputs 177 of microneedles 173 and is dispensed into the dermal layer of the patient. It can be appreciated that upon release of pushbutton 70, resilient material from which depression 60 is fabricated causes upper wall 52 to return to its original configuration, FIGS. 4-5.

It is noted that the rate of expansion of hydrogel pressure source 138 controls the flow rate of the drug from chamber 140 into the patient. Hence, desired delivery profiles such as bolus injections, constant infusion, delayed onset or the like are possible simply by altering the chemistry of hydrogel pressure source 138. It is also noted that the array of microneedles 172 can be replaced with a single microneedle 173 or like without deviating from the scope of the present invention. Further, docking station 154 and/or the array of microneedles 172 may be integrally formed with rigid bladder member 110

Various modes of carrying out the invention are contemplated as being within the scope of the following claims particularly pointing and distinctly claiming the subject matter that is regarded as the invention.

We claim:

1. A bladder arrangement for an active transdermal drug delivery device, comprising:
    a first flexible membrane having an inner and outer surface;
    a bladder member including an inner surface, an outer surface and an aperture therethrough, the inner surface of the flexible membrane and the inner surface of the bladder member defining a chamber for receiving a drug therein;
    an array of microneedles, each microneedle having an input;
    a valve arrangement received within the aperture in the bladder member and communicating with the inputs of the microneedles through a passageway, the valve arrangement movable between a first configuration wherein the inputs of the microneedles are isolated from the drug in the chamber and a second configuration wherein the passageway communicates with the drug in the chamber;
    a pressure source engageable with the flexible membrane, the pressure source having a first retracted configuration and a second expanded configuration wherein the pressure source urges the drug from the chamber towards the passageway; and
    an actuator movable between a first non-actuated position and a second actuated position; wherein:
    the pressure source moves to the expanded configuration in response to the movement of the actuator to the actuated position;
    the valve arrangement moves from the first configuration to the second configuration in response to the movement of the actuator to the actuated position; and
    at least a portion of the bladder member defining the aperture is rigid.

2. The bladder arrangement of claim 1 wherein:
    the first flexible membrane has an outer periphery;
    the bladder member has an outer periphery; and
    the outer periphery of the first flexible membrane and the outer periphery of the bladder member are bonded to form a hermetic seal.

3. The bladder arrangement of claim 1 wherein the bladder member includes an opening therethrough for allowing the drug to be injected into the chamber and wherein the bladder arrangement further comprises a plug receivable in the opening in the bladder matter for maintaining the drug in the chamber.

4. The bladder arrangement of claim 1 wherein the valve arrangement includes a check valve, the check valve allowing the drug to flow in a first direction from the chamber to the passageway and preventing fluid flow in a second direction from the passageway to the chamber.

5. A bladder arrangement for a drug delivery device, comprising:
    a flexible membrane having an inner surface, an outer surface and an outer periphery;
    a bladder member including an inner surface, an outer surface, an aperture extending therethrough and an outer periphery bonded to the outer periphery of the flexible membrane, the inner surface of the flexible membrane and the inner surface of the bladder member defining a chamber for receiving a drug therein;
    an array of microneedles, each microneedle having an input communicating with a passageway; and
    a valve arrangement received in the aperture for controlling the flow of the drug from the chamber to the passageway, the valve arrangement movable between a first configuration wherein the inputs of the microneedles are is isolated from the drug in the chamber and a second configuration wherein the passageway communicates with the drug in the chamber;
    a pressure source engageable with the flexible membrane, the pressure source having a first retracted configuration and a second expanded configuration wherein the pressure source urges the drug from the chamber towards the passageway; and
    an actuator movable between a first non-actuated position and a second actuated position; wherein:
    the pressure source moves to the expanded configuration in response to the movement of the actuator to the actuated position;
    the valve arrangement moves from the first configuration to the second configuration in response to the movement of the actuator to the actuated position; and
    at least a portion the bladder member defining the aperture is rigid.

6. The bladder arrangement of claim 5 wherein the outer periphery of the flexible membrane and the outer periphery of the bladder member are bonded to form a hermetic seal.

7. The bladder arrangement of claim 5 wherein the bladder member includes an opening therethrough for allowing the drug to be injected into the chamber and wherein the bladder arrangement further comprises a plug receivable in the opening in the bladder matter for maintaining the drug in the chamber.

8. The bladder arrangement of claim 5 wherein the valve arrangement includes a check valve, the check valve allowing the drug to flow in a first direction from the chamber to the passageway and preventing fluid flow in a second direction from the passageway to the chamber.

9. The bladder arrangement of claim 5 wherein the pressure source includes an expandable hydrogel, the hydrogel applying pressure on the flexible member as the hydrogel expands.

10. A bladder arrangement for a drug delivery device, comprising:
    a flexible membrane having an inner surface, an outer surface and an outer periphery;
    a bladder member having an aperture therethough and including an inner surface, an outer surface and an outer periphery, the inner surfaces of the flexible membrane and the inner surface of the bladder member defining a chamber for receiving a drug therein;
    an array of microneedles having inputs communicating with a passageway and outputs receivable within the individual; and
    a valve received in the aperture in the bladder member and operatively connecting the passageway and the chamber, the valve movable between a first configuration wherein the inputs of the microneedles are is isolated from the drug in the chamber and a second configuration wherein the passageway communicates with the drug in the chamber;

a pressure source engageable with the flexible membrane, the pressure source having a first retracted configuration and a second expanded configuration wherein the pressure source urges the drug from the chamber towards the passageway; and an actuator movable between a first non-actuated position and a second actuated position; wherein:

the pressure source moves to the expanded configuration in response to the movement of the actuator to the actuated position;

the valve moves from the first configuration to the second configuration in response to the movement of the actuator to the actuated position; and the entirety of the bladder member is rigid.

11. The bladder arrangement of claim 10 wherein the outer periphery of the flexible membrane and the outer periphery of the bladder member are bonded to form a hermetic seal.

12. The bladder arrangement of claim 10 wherein the bladder member includes an opening therethrough for allowing the drug to be injected into the chamber and wherein the bladder arrangement further comprises a plug receivable in the opening in the bladder member for maintaining the drug in the chamber.

13. The bladder arrangement of claim 10 wherein the valve is a check valve, the check valve allowing the drug to flow in a first direction from the chamber to the passageway and preventing fluid flow in a second direction from the passageway to the chamber.

14. The bladder arrangement of claim 10 further comprising a docking station for supporting the array of microneedles, the docking station being removably connected to the bladder member.

* * * * *